US00PP13295P3

(12) United States Plant Patent

Olesen et al.

(10) Patent No.: US PP13,295 P3
(45) Date of Patent: Dec. 3, 2002

(54) HYBRID TEA ROSE PLANT NAMED 'POULGRENA'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/774,823

(22) Filed: Jan. 30, 2001

(65) Prior Publication Data

US 2002/0152517 P1 Oct. 17, 2002

(51) Int. Cl.[7] ..... A01H 5/00
(52) U.S. Cl. ..... Plt./135
(58) Field of Search ..... Plt./135

(56) References Cited

PUBLICATIONS

UPOV–ROM GTITM Computer Database, 2001/06, GTI Jouve Retrieval Software, citation for 'Poulgrena'.*

* cited by examiner

*Primary Examiner*—Bruce R. Campell
*Assistant Examiner*—Susan B. McCormick

(57) ABSTRACT

A new garden rose plant which has abundant, orange flowers and attractive foliage. This new and distinct variety has shown to be uniform and stable in the resulting generations from asexual propagation.

1 Drawing Sheet

SUMMARY OF THE INVENTION

The present discovery constitutes a new and distinct variety of a Hybrid Tea rose plant which was discovered in a cultivated area. The mutation resulted from 'POULrim', a Hybrid Tea rose hybridized by the same inventors. 'POULrim' is described and illustrated in U.S. Plant patent application Ser. No. 09/277,236, dated Mar. 26, 1999. The new rose variety resulted from a naturally occurring mutation of unknown causation on a branch of 'POULrim'.

The rose plant of the present discovery has a unique combination of characteristics which are outstanding in the new variety and which distinguish it from the original rose 'POULrim' as well as all other varieties which we are aware of. For example, the new variety has:

1. Abundant, striking orange flowers;
2. Above average disease resistance;
3. Repeat blooming;
4. Vigorous, dark glossy green foliage; and
5. Perfumed rose scent.

This combination of qualities is not present in previously available commercial cultivars of this type and distinguish 'POULgrena' from all other varieties of which we are aware. The resulting mutation was selected in spring 1998 and evaluations were conducted on the resulting rose plants in a controlled environment.

Asexual reproduction of 'POULgrena' by cuttings was first done by L. Pernille and Mogens N. Olesen in Fredensborg, Denmark, in August, 1998. This initial and other subsequent propagations have demonstrated that the characteristics of 'POULgrena' are true to type and are transmitted from one generation to the next.

BRIEF DESCRIPTION OF THE DRAWING

The accompanying color illustration shows as true as is reasonably possible to obtain in color photographs of this type, the typical characteristics of 'POULgrena', potted rose plant. Specifically illustrated in SHEET 1 are 'POULgrena's' foliage, flower buds, partially opened buds, and a flower bloom.

DETAILED DESCRIPTION OF THE VARIETY

The following is a description of 'POULgrena', as observed in its growth during trials at the testing station Prüfstelle Rethmar, under the testing authority Bundessortenamtin in Hannover, Germany and the breeder's nursery in Fredensborg, Denmark. Color references are made using The Royal Horticultural Society (London, England) Colour Chart, 1995, except where common terms of color are used.

For a comparison, several physical characteristics of the rose variety 'POULrim', a rose variety from the same inventors described and illustrated in U.S. Plant patent application Ser. No. 09/277,236 dated Mar. 26, 1999 are compared to 'POULgrena' in Chart 1.

CHART 1

| | 'POULgrena' | 'POULrim' |
|---|---|---|
| Color of open bloom, outer petals | Orange Group 24C to Orange-Red Group 32C | Yellow-Orange Group 20B |
| Size of petal spot of open bloom, outer side | Medium | Very small |
| Plant size | 50–80 cm (h) × 50 cm (w) | 90 cm (h) × 75 cm (w) |

Parents: Mutation of 'POULrim'.
Classification:
*Botanical.*—*Rosa hybrida.*
*Commercial.*—Hybrid tea.

FLOWER AND FLOWER BUD

Blooming habit: Recurrent.
Flower bud:
*Size.*—Upon opening, 28–30 mm in length from base of receptacle to end of bud. Diameter is 50 mm.

*Bud form.*—Pointed ovoid.

*Bud color.*—Orange-Red Group 34A–B at ¼ opening.

*Sepals.*—Yellow-Green Group 144B. Anthocyanin present on 2–3 sepals of Greyed-Purple Group 183C. Weak foliaceous appendages on three of the five sepals. Surfaces of sepals slighty pubescent. A limited number of stipitate glands are present along sepal margins. Sepals are 30 to 40 mm long and 10 to 13 mm wide.

*Receptacle.*—Surface: Smooth. Shape: Pitcher shape. Size: Small. 7–8 mm (h)×12 mm (w). Color: Yellow-Green Group 144C.

*Peduncle.*—Surface: Moderate number of hairs and prickles. Length: 90–130 mm average length. Color: Yellow-Green Group 144B with anthocyanin observed in tone of Greyed-Purple Group 183B–C. Strength: Upright. Diameter: 7 mm.

*Borne.*—Generally singly. Occasionally with up to five buds per flowering stem.

Flower bloom:

*Fragrance.*—Very perfumed rose scent.

*Duration.*—As a cut flower 3 to 5 days. The blooms have a duration on the plant of approximately 6 to 7 days.

*Size.*—Medium to large for a hybrid tea rose. Average flower diameter is 100–120 mm when open.

*Form.*—Shape of flower when viewed from the side: Upon opening, upper part: Convex. Upon opening, lower part: Flat. Open flower, upper part: Flat to Flattened Convex. Open flower, lower part: Flat.

*Petalage.*—Double, with 25–30 petals under normal conditions with 1–3 petaloids.

Color:

*Upon opening, petals.*—Outermost petals: Inner Side: Orange-Red Group 30B. Outer Side: Orange Group 24C to Orange-Red Group 32C. Innermost petals: Inner Side: Orange-Red Group 30B. Outer Side: Orange Group 24C to Orange-Red Group 32C.

*Upon opening, basal petal spots.*—Outermost petals: Outer Side: Yellow Group 9C. Inner Side: Yellow Group 9B. Innermost petals: Outer Side: Yellow Group 9C. Inner Side: Yellow Group 9B.

*After opening, petals.*—Outermost petals: Margins of upper surface exhibit intonations of Orange-Red Group 30B–30A. Inner Side: Orange-Red Group 30B. Outer Side: Orange Group 24C to Orange-Red Group 32C. Innermost petals: Inner Side: Orange-Red Group 30B. Outer Side: Orange Group 24C to Orange-Red Group 32C.

*After opening, basal petal spots.*—Outermost petals: Outer Side: Yellow Group 9C. Inner Side: Yellow Group 9B. Innermost petals: Outer Side: Yellow Group 9C. Inner Side: Yellow Group 9B.

General tonality: On open flower blend of Yellow-Orange Group 24C to Orange-Red Group 32C.

Petals:

*Petal reflex.*—Petals reflexed. Outermost petals double reflexed.

*Petal edge.*—Undulating.

*Shape.*—Round to deltoid. Apex is rounded, base is acute.

*Petaloids.*—1–3 petaloids.

*Thickness.*—Average.

*Arrangement.*—Imbricated.

*Texture.*—Smooth.

*Size.*—Petals are 35 mm long and 35 mm wide.

Reproductive organs:

*Pollen.*—Color: Yellow-Orange Group 14B. Quantity: Average.

*Anthers.*—Size: Medium. Color: Immature: Green-Yellow Group 1B. Margins Greyed-Red Group 180A. Mature: Brown Group 200A. Quantity: Average.

*Filaments.*—Color: Yellow-Orange Group 14B. Quantity: 25 to 30.

*Stigmas.*—Located at same level as anthers. Color: Yellow-Green Group 145D.

*Styles.*—Quantity: Color: Green-White Group 157A.

*Other intonations.*—Below stigma, Red-Purple Group 57C.

*Hips.*—None observed.

PLANT

Plant growth: Vigorous, upright to bushy. When grown as a budded field grown plant on multiflora understock, the average height of the plant itself is 50–80 cm and the average width is 50 cm.

*Roots.*—Root initials are apparent 8 days after planting; roots begin to develop 10 to 14 days after planting.

Stems:

*Color.*—Young wood: Green Group 143A. Older wood: Green Group 138A.

*Thorns.*—Incidence: Moderate to thorny with many long prickles. Size: Average length: 6–8 mm. Color: Yellow-Green Group 144C–D. Some intonations of Greyed-Red Group 178B. Shape: Concave.

*Surface.*—Young wood: Smooth. Older wood: Smooth.

*Length.*—35 to 40 mm.

*Diameter.*—8 mm.

Plant foliage: Normal number of leaflets on leaves in middle of the stem: 5 leaflets.

*Leaf size.*—Medium to large. 120–130 mm (l)× 110–120 mm (w).

*Quantity.*—Very abundant.

*Color.*—Upper Leaf Surface: Green Group 147A. Lower Leaf Surface: Green Group 138A–B.

*Juvenile foliage.*—Upper Leaf Surface: Green Group 137A. Lower Leaf Surface: Green Group 138A.

*Anthocyanin.*—Medium to strong intonations on all new growth. Location: Leaflets (upper and lower), stems, petiole and sepals. Color: Greyed-Purple Group 183B.

Plant leaves and leaflets:

*Stipules.*—Size: 15–20 mm. Color: Green Group 143A.

*Stipitate glands.*—On margins of stipules.

*Petiole.*—Length: 25–30 mm. Color: Green Group 137A. Underneath: With several small prickles. Margins: Stipitate glands present. Diameter: 3 mm.

*Rachis.*—Color: Green Group 137A. Underneath: With several small prickles. Margins: Stipitate glands present.

*Leaflet.*—Edge: Serrated. Shape: Ovate; apex is acute, base is rounded. Texture: Glossy. Strong and leathery. Size: 25 mm (w)×45 mm (l).

*Arrangement.*—Odd pinnate.

*Venation.*—Reticulate.

Disease resistance: Above average resistance to mildew, rust, black spot, and Botrytis under normal growing conditions in Fredensborg, Denmark and Hannover, Germany.

Cold hardiness: The variety 'POULgrena' has been found to be cold hardy in Fredensborg, Denmark and Hannover, Germany.

We claim:

1. A new and distinct variety of rose plant of the Hybrid Tea class, substantially as herein illustrated and described as a distinct and novel rose variety due to its abundant orange flowers, disease resistance, and extended period of bloom.

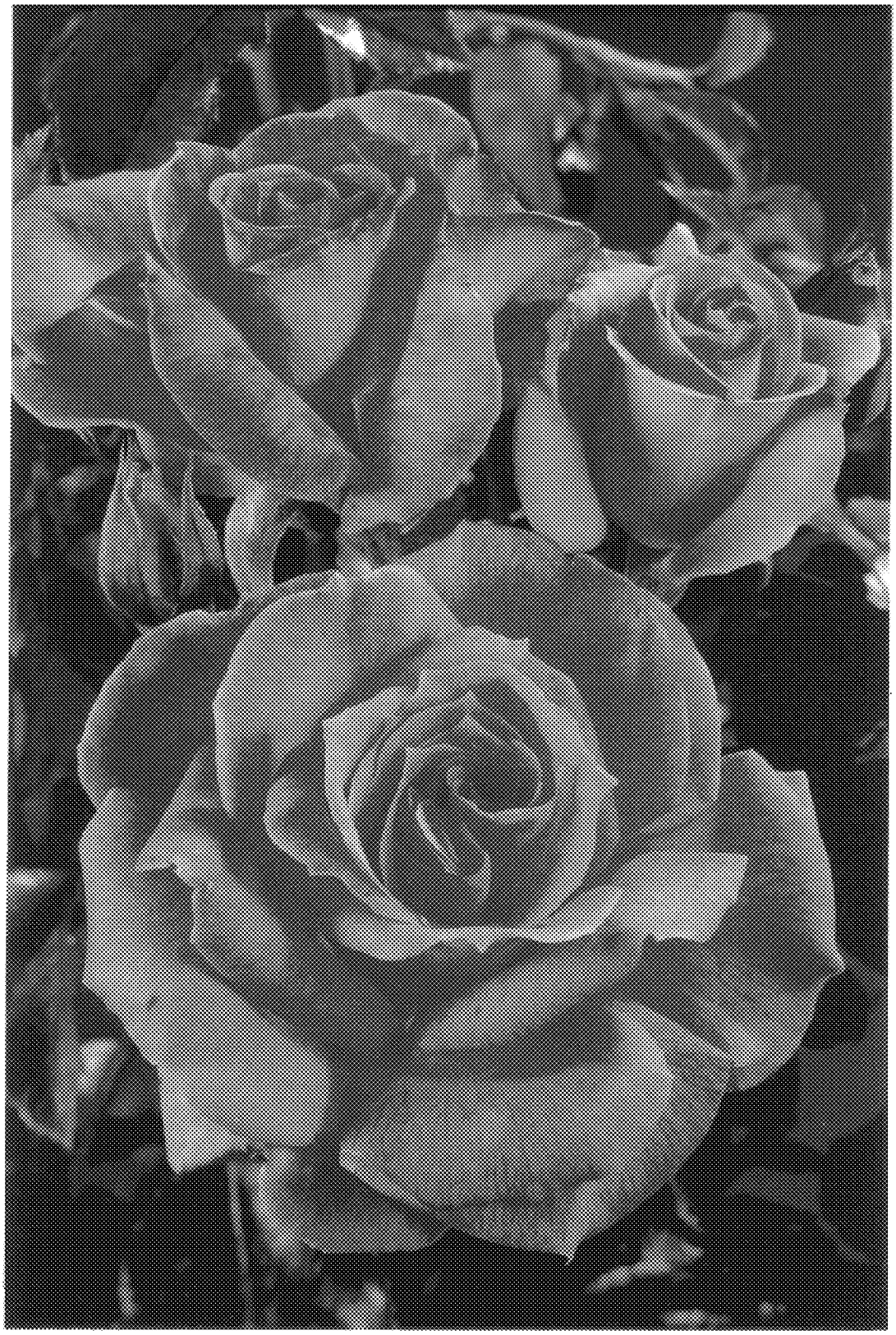

* * * * *